(12) United States Patent
Behler et al.

(10) Patent No.: US 10,201,487 B2
(45) Date of Patent: Feb. 12, 2019

(54) HAIR COSMETIC COMPOSITION WHICH COMPRISES A PLANT LECITHIN

(71) Applicant: BASF SE, Ludwigshafen (DE)

(72) Inventors: Ansgar Behler, Bottrop (DE); Sybille Cornelsen, Ratingen (DE); Detlev Stanislowski, Mettmann (DE); Monika Barbenheim, Bottrop (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/389,819

(22) PCT Filed: Mar. 22, 2013

(86) PCT No.: PCT/EP2013/056038
§ 371 (c)(1),
(2) Date: Oct. 1, 2014

(87) PCT Pub. No.: WO2013/149853
PCT Pub. Date: Oct. 10, 2013

(65) Prior Publication Data
US 2015/0071867 A1   Mar. 12, 2015

Related U.S. Application Data

(60) Provisional application No. 61/619,451, filed on Apr. 3, 2012.

(30) Foreign Application Priority Data

Apr. 3, 2012  (EP) .................................. 12163002

(51) Int. Cl.
| | | |
|---|---|---|
| A61K 8/44 | (2006.01) | |
| A61Q 5/04 | (2006.01) | |
| A61Q 5/12 | (2006.01) | |
| A61Q 5/06 | (2006.01) | |
| A61Q 5/02 | (2006.01) | |
| A61K 8/34 | (2006.01) | |
| A61K 8/46 | (2006.01) | |
| A61K 8/55 | (2006.01) | |
| A61K 8/97 | (2017.01) | |

(52) U.S. Cl.
CPC ............... *A61K 8/463* (2013.01); *A61K 8/34* (2013.01); *A61K 8/44* (2013.01); *A61K 8/46* (2013.01); *A61K 8/55* (2013.01); *A61K 8/553* (2013.01); *A61K 8/97* (2013.01); *A61Q 5/02* (2013.01); *A61Q 5/04* (2013.01); *A61Q 5/06* (2013.01); *A61Q 5/12* (2013.01); *A61K 2800/10* (2013.01)

(58) Field of Classification Search
None
See application file for complete search history.

(56) References Cited

U.S. PATENT DOCUMENTS

| | | |
|---|---|---|
| 4,174,296 A | 11/1979 | Kass |
| 4,237,253 A | 12/1980 | Jacquet et al. |
| 4,814,101 A | 3/1989 | Schieferstein et al. |
| 5,880,252 A | 3/1999 | Kim et al. |
| 8,357,381 B2 | 1/2013 | Eskuchen et al. |
| 2004/0043405 A1 | 3/2004 | Seipel et al. |
| 2004/0197276 A1* | 10/2004 | Takase et al. ................... 424/47 |
| 2006/0248660 A1* | 11/2006 | Ryan et al. ....................... 8/405 |
| 2010/0034893 A1* | 2/2010 | Pfluecker et al. ............ 424/490 |
| 2013/0251661 A1 | 9/2013 | Falkowski et al. |

FOREIGN PATENT DOCUMENTS

| | | |
|---|---|---|
| DE | 2150557 | 6/1972 |
| DE | 2817369 | 10/1978 |
| DE | 3708451 | 10/1988 |
| DE | 3929973 | 3/1991 |
| DE | 4333238 | 4/1995 |
| DE | 10-2006-035040 | 1/2008 |
| EP | 0983041 | 3/2000 |
| EP | 1146854 | 10/2001 |
| EP | 1183008 | 3/2002 |
| EP | 1430870 | 6/2004 |
| GB | 1368495 | 9/1974 |
| JP | S50070410 A | 6/1975 |
| JP | 60-094903 | 5/1985 |
| JP | S61054231 A | 3/1986 |
| JP | H9301834 A | 11/1997 |
| JP | 2002370945 A | 12/2002 |
| JP | 2014505799 A | 3/2014 |
| WO | WO-98/56333 | 12/1998 |
| WO | WO-00/33808 | 6/2000 |
| WO | WO-00/74644 | 12/2000 |
| WO | WO-02/34216 | 5/2002 |
| WO | WO-2007/124864 | 11/2007 |

OTHER PUBLICATIONS

Jojoba Hair Repair Mask, *Mintel*, XP-002688506, Record ID: 1666386 Nov. 2011, 3 pages.
Official Journal of the European Union, L 253, vol. 51 Sep. 20, 2008, 5 pages.
PCT International Preliminary Report on Patentability in PCT/EP2013/056038, dated Oct. 7, 2014, 9 pages.
PCT International Search Report and Written Opinion in PCT/EP2013/056038, dated Mar. 18, 2014, 12 pages.
Shine & Volume Conditioner, *Mintel*, XP-002688505, Record ID: 1447146 Dec. 2010, 1 page.
Lanteri, A., Session IV: Processing and Packaging—Sulfonation and Sulfation Technology, *J. Am. Oil Chemists' Soc.*, vol. 55 Jan. 1978, 128-133.
Lendrath, G., et al., Behaviour of vegetable phospholipids in thin-layer chromatography: Optimization of mobile phase, detection and direct evaluation, *Journal of Chromatography* vol. 502 1990, 385-392.
Takehara, Masahiro, et al., Surface Active N-Acylglutamate: II. Physicochemical Properties of Long Chain N-Acylglutamic Acids and Their Sodium Salts, *Journal of the American Oil Chemists' Society*, vol. 49 Mar. 1972, 143-150.
Product Data Sheet: BioBase EP, *Oberhausen Technology Center* Jan. 2010, 2 pages.
Notice of Reasons for Rejection, Japanese patent application No. 2015-503816, dated Mar. 21, 2017.

\* cited by examiner

*Primary Examiner* — David J Blanchard
*Assistant Examiner* — Sarah J Chickos
(74) *Attorney, Agent, or Firm* — Marshall, Gerstein & Borun LLP

(57) ABSTRACT

Described is a hair cosmetic composition which comprises at least one plant lecithin, at least one anionic surfactant, and at least one fatty alcohol.

4 Claims, No Drawings

HAIR COSMETIC COMPOSITION WHICH COMPRISES A PLANT LECITHIN

CROSS-REFERENCE TO RELATED APPLICATIONS

This application is the National Stage entry of PCT/EP2013/056038, filed on Mar. 22, 2013, which claims priority to European Application Number 12163002.4, filed on Apr. 3, 2012, and U.S. Provisional Application Ser. No. 61/619,451 filed on Apr. 3, 2012, which are incorporated herein by reference in their entireties.

TECHNICAL FIELD

The present invention relates to a hair cosmetic composition which comprises at least one plant lecithin, at least one anionic surfactant, and at least one fatty alcohol.

BACKGROUND

Hair is subjected to a wide variety of severe stress, for example as a result of environmental influences, such as UV irradiation or weathering, mechanical stresses, such as combing, or various hair treatments, such as washing, drying with hot air, bleaching, coloring, perming, etc., which can lead to hair damage. Said damage includes e.g. dryness, reduced elasticity, brittleness, split ends, dullness, matte appearance, reduced fullness, rough surface and reduced mechanical strength. This leads to impaired combability, reduced shine, increased electrostatic charging and tendency to break. The hair wearer feels uneasy.

There is therefore a need for hair cosmetic compositions with a complex profile of properties which counteract the negative effects of stressed hair in as diverse a manner as possible. They should be characterized by good conditioning, care, protective and hair-damage repairing properties. Also of importance is good formulatability of the components used, which must be characterized by high compatibility. Moreover, the finished products should have good application properties. These often include e.g. a good thickening effect, the intention being to use additional thickeners to the lowest possible extent.

Moreover, the consumer nowadays often prefers "green" products, for the manufacture of which as many components of "natural" origin as possible are used, and components with an environmental impact are to be dispensed with. The expectations of many consumers, especially in Europe, of a natural product also comprises that in the case of the raw materials, the use of genetically modified components should be dispensed with as far as possible.

Conditioners known from the prior art often comprise cationic surfactants and/or cationic hair polymers. These attach to the hair and lead to an improvement in combability and shine of the hair, the polymers, at the same time, often improving the consistency of these preparations. Although cationic surfactants, such as e.g. cetyltrimethylammonium chloride (CTAC) or bephenyl trimethylammonium chloride (BTAC), generally have good conditioning properties, on account of their poor biodegradability, they are not consistent with use in a "natural" hair conditioner. Moreover, cationic surfactants and polymers, depending on the composition of the overall formulation in which they are used, also have some disadvantages under certain circumstances. For example, the sensory behavior of such conditioners on the hair is in some cases in need of improvement, which can become noticeable from a coated, slippery, but also sometimes harsh, somewhat sticky feel to the touch.

Furthermore, silicone oils and/or hair polymers containing silicone groups are often used in conditioning hair cosmetic compositions. The desired effects when using silicone are e.g. the generation of shine, improvement in the combability or the enclosure of split ends or other kind of hair damage (especially in repair shampoos). However, due to various properties, the use of silicones in a "natural" hair conditioner is undesired. For example, hair damage is often merely concealed by silicone-containing conditioners and not permanently repaired. The actual condition of the hair under the silicone is no longer evident, and targeted compensating care becomes difficult. Moreover, especially water-insoluble silicones have a tendency to "build-up" on the hair, and the hair becomes heavy and lifeless. Under the silicone layer, the hair can dry out unnoticed, which can lead to increased split ends and hair breakage.

Conditioning hair cosmetic compositions are therefore sought, for the manufacture of which the use of cationic surfactants and/or silicone compounds can be reduced or avoided.

EP 0 983 041 A1 describes an aqueous carrier system for water-insoluble materials which comprises at least one phospholipid which is capable of forming vesicles, at least one amphoteric surfactant and at least one non-ionic surfactant.

EP 1 183 008 A1 has a disclosure content comparable to that of EP 0 983 041 A1.

EP 1 430 870 A2 describes a hair cosmetic composition which comprises at least one lecithin, at least one amphoteric surfactant, at least one non-ionic surfactant, at least one film forming polymer and at least one cationic polymer.

EP 1 146 854 B1 describes a composition which comprises at least one organic phospholipid which is capable of forming vesicles, at least one amphoteric surfactant and at least one non-ionic surfactant. It can be used as dosage form for waxes, water-insoluble polymers, resins and lattices.

DE 102006035040 A1 describes an active ingredient combinations of a) one or more active ingredients from the group of ascorbic acid and of ascorbyl compounds and b) mixtures of a $C_{12}$-$C_{16}$-alcohol, hydrogenated lecithin and palmitic acid.

WO 2007/124864 describes a dispersion which comprises water, a lipophilic phase and an emulsifier, the emulsifier comprising at least one acyl glutamate. Merely optionally the dispersion can additionally also comprise a phospholipid. A use of these dispersions in a hair cosmetic composition, specifically a hair conditioner, is not described.

Accordingly, there is a need for an improved composition for conditioning hair treatment compositions. The composition should be suitable for covering a complex spectrum of requirements, as described at the start. In particular, it is desired to provide hair conditioners regarded by the consumer as being "natural", which have good conditioning properties, are comparable with conditioners based on cationic surfactants and/or silicone compounds known from the prior art.

SUMMARY

A first aspect of the invention provides a hair cosmetic composition comprising
a) at least one plant lecithin,
b) at least one anionic surfactant, and
c) at least one fatty alcohol.

A second aspect of the invention further provides the use of a composition which comprises components a), b) and c)

in a hair treatment composition, in particular in a conditioning hair treatment composition.

A third aspect of the invention further provides a solid composition which consists of components a), b) and c).

A fourth aspect of the invention further provides the use of such a solid composition as intermediate for producing a hair cosmetic composition.

DETAILED DESCRIPTION

Surprisingly, it has been found that a composition, which comprises at least one plant lecithin, at least one anionic surfactant, and at least one fatty alcohol is suitable for covering a complex spectrum of requirements, such as providing hair conditioners regarded by the consumer as being "natural", which have good conditioning properties, are comparable with conditioners based on cationic surfactants and/or silicone compounds known from the prior art.

The hair cosmetic composition according to one or more embodiments of the invention has at least one of the following advantages:
improvement in the dry and wet combability of the hair,
improvement in the detangleability of the hair,
good styling properties,
improvement in the feel to the touch,
improvement in the shine,
reduction in electrostatic charging,
reduction in tendency toward split ends,
improvement in hair fullness,
protection of the hair during chemical hair treatments,
realization of a natural ("green") conditioner concept,
no tendency to form discolorations and/or unpleasant odor.

Surprisingly, it has also been found that components a), b) and c) used according to the invention are suitable for formulating a solid composition which consists of these components and which is suitable as an intermediate in the form of an easy-to-handle formulation basis for the ultimate marketing form.

Component a)

In one or more embodiments, the composition comprises component a) in an amount of from 4 to 60% by weight, particularly 10 to 50% by weight, in particular 15 to 40% by weight, based on the total weight of components a), b) and c).

As used herein, the term lecithin is not limited to phosphatidylcholine, but refers to a complex substance mixture of polar, acetone-insoluble (main component: phospho- and glycolipids), nonpolar, acetone-soluble lipids (main component: triglycerides) and further ingredients. This definition is in agreement with the description by the EU for lecithins in the food sector (E 322, see Official Journal of the European Union L 253/39 dated Sep., 20, 2008).

As used herein, the term lecithin also includes lecithin which has been subjected to at least one work-up step. Suitable work-up steps comprise deoiling and/or fractionation. In the case of deoiling, the oil and/or the free fatty acids is/are removed from the native lecithin. Deoiling serves to produce pulverulent or granulated, so-called "pure lecithins". These have a phospholipid concentration that is increased compared to native lecithins and generally have improved O/W emulsifying properties.

In one or more embodiments, fractionation of lecithin comprises a single-stage or multistage extraction with an organic solvent or solvent mixture. For the extraction, preference is given to using an alcohol or a hydrocarbon or hydrocarbon mixture, in particular ethanol or hexane. Fractionation of the lecithin then comprises separation into at least one fraction that is soluble in the extractant and at least one fraction that is insoluble in the extractant. Instead of or in addition to extractive fractionation, it is possible to use customary chromatographic methods for the fractionation.

As used herein, the term lecithin also includes lecithin which has been subjected to at least one chemical modification step. In one or more embodiments, the modification is selected from enzymatic hydrolysis, acetylation, hydroxylation, hydrogenation, or a combination of at least two of the aforementioned processes. Enzymatic modification is based on separating off a fatty acid molecule from the phospholipid molecule with the help of a phospholipase. Acetylation is a modification of the phosphatidylethanolamine present in the lecithin by acylation of the amino group with an acetyl radical. Hydroxylation of the mono- and polyunsaturated fatty acids bonded in the phospholipid molecule can take place for example by reaction with hydrogen peroxide. Hydrogenation of the mono- and polyunsaturated fatty acids bonded in the phospholipid molecule can take place for example by reaction with hydrogen in the presence of customary hydrogenation catalysts.

Standard commercial lecithin is a composition which comprises primarily phospholipids, as well as glycolipids, triglycerides and concomitant substances (such as sterols, free fatty acids, tocopherols, phenolic acids, sinapine, etc.), and also small amounts of carbohydrates.

In one or more embodiments, the lecithin used according to the invention as component a) has a total phospholipid content of at least 35% by weight, particularly at least 38% by weight, in particular at least 40% by weight, based on the total weight of component a).

In one or more embodiments, the lecithin used according to the invention as component a) has a neutral lipid content (i.e. acetone-soluble lipids) of at least 20% by weight, particularly at least 25% by weight, based on the total weight of component a).

In one or more embodiments, the lecithin used according to the invention as component a) has an iodine number of at least 10. The iodine number is a measure of the content in lecithin component a) of unsaturated compounds and refers to the amount of iodine in grams which can be formally added to 100 grams of lecithin component a).

In one or more embodiments, the lecithin used according to the invention as component a) has an oleic acid content after cleavage of at least 35% by weight, particularly at least 40% by weight, based on the total weight of component a). The oleic acid content after cleavage refers here to component a) after separating off one molecule of fatty acid from the phospholipid molecule. This takes place for example via an enzymatic hydrolysis, e.g. with the help of the phospholipase A2.

In one or more embodiments, the lecithin used as component a) has a quantitative weight ratio of phosphatidylcholine to phosphatidylethanolamine of $\geq 1$.

Plant lecithins suitable as component a) are selected from rapeseed lecithin, soya lecithin, corn lecithin, sunflower lecithin and mixtures thereof.

In a specific embodiment, component a) comprises no lecithin from genetically modified plants. This proviso can be satisfied by using rapeseed lecithin since, at least in the EU, no genetically modified rapeseed plants are currently approved for cultivation.

In one or more embodiments, component a) consists, to at least 30% by weight, particularly to at least 50% by weight, in particular to at least 75% by weight, specifically to at least 90% by weight, based on the total weight of component a), of rapeseed lecithin. In a specific embodiment, exclusively rapeseed lecithin is used as component a).

Compared with other plant lecithins, and specifically soya lecithin, the use of rapeseed lecithin has the following additional advantages:
- particularly advantageous rheological properties can be achieved, meaning that, to produce viscous formulations, the use of thickeners can be reduced or avoided,
- the use of genetically modified material can, if desired, easily be avoided (different to e.g. in the case of soya lecithin),
- rapeseed is an indigenous oil plant.

The term "rapeseed" generally refers to oil seeds which originate from the plant genus *Brassica* (cabbage plants). Of suitability in principle for obtaining rapeseed lecithin are the various rapeseed cultures available worldwide, e.g. the plant varieties *Brassica carinata, Brassica juncea, Brassica. rapa* and *Brassica napus*. A rapeseed variety cultivated specifically in central Europe is winter rapeseed (*Brassica napus* L.).

A comprehensive description of the composition and functionality of lecithin from rapeseeds can be found in the Dissertation by Claudia Heift, Institute for Biochemistry and Food Chemistry, University of Hamburg, 2007.

Rapeseed lecithin suitable as component a) has, for example, the following composition:
triglycerides: 18-40%
phospholipids total: 38-52%
phosphatidylcholine: 13-17%, preferably 14-16%
phosphatidylethanolamine: 6-10%
phosphatidylinositol: 9.0-11.5%
phosphatidic acid: 2-6%
glycolipids total: 6-10%
steryl glycosides: 4-6%
digalactosyl diacylglycerols: 2-4%
cerebrosides: 0.5-1.5%
carbohydrates: 3-12%
Concomitant substances total: 0.5-5%
α-tocopherol: 10-2500 ppm
sterols, phenolic acids (sinapine), chlorophyll, etc.

In one or more embodiments, the rapeseed lecithin used as component a) has a triglyceride fraction in the range from 32% to 42%. An essential difference between rapeseed lecithin on the one hand and soya or sunflower lecithin on the other hand lies in the fatty acid composition. For example, rapeseed lecithin has a higher fraction of oleic acid and a lower fraction of linoleic acid.

The following table shows the fraction of $C_{16}$- and $C_{18}$-fatty acids of a rapeseed lecithin suitable as component a), based on the total fatty acid content:
palmitic acid: 4-8% by weight
stearic acid: 0.5-3% by weight
oleic acid: 35-45% by weight
linoleic acid: 12-22% by weight
linolenic acid: 2-5% by weight.

A commercially available rapeseed lecithin suitable for use as component a) is Solec RF-10 from Solae Europe S.A., Ouderkerke a.d. Ijssel, NL.

Component b)

In one or more embodiments, the composition according to the invention comprises component b) in an amount of from 1 to 30% by weight, particularly 2 to 25% by weight, in particular 3 to 20% by weight, based on the total weight of components a), b) and c).

Typical examples of anionic surfactants are soaps, alkylsulfonates, alkylbenzenesulfonates, olefinsulfonates, alkyl ether sulfonates, glycerol ether sulfonates, methyl ester sulfonates, sulfo fatty acids, alkyl sulfates, fatty alcohol ether sulfates, glycerol ether sulfates, fatty acid ether sulfates, hydroxyl mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ethercarboxylic acids and salts thereof, fatty acid isethionates, fatty acid sarcosinates, fatty acid taurides, N-acylaminoacids, such as, for example, acyl lactylates, acyl tartrates, acyl glutamates and acyl aspartates, alkyl oligoglucosidesulfates, alkyl glucose carboxylates, protein fatty acid condensates and alkyl (ether)phosphates.

In one or more embodiments, component b) comprises at least one acyl glutamate or at least one alkyl sulfate.

Suitable soaps are e.g. alkali metal, alkaline earth metal and ammonium salts of fatty acids, such as potassium stearate.

Suitable olefinsulfonates are obtained e.g. by the addition reaction of $SO_3$ onto olefins of the formula $R^3$—CH=CH—$R^4$ and subsequent hydrolysis and neutralization, where $R^3$ and $R^4$, independently of one another, are H or alkyl radicals having 1 to 20 carbon atoms, with the proviso that $R^3$ and $R^4$ together have at least 6 and preferably 8 to 20, specifically 10 to 16, carbon atoms. As regards preparation and use, reference may be made to the overview article "J. Am. Oil. Chem. Soc.", 55, 70 (1978). The olefinsulfonates can be present as alkali metal, alkaline earth metal, ammonium, alkylammonium, alkanolammonium or glucammonium salts. Preferably, the olefinsulfonates are present as sodium salts. The hydrolyzed alpha-olefin-sulfonation product, i.e. the alpha-olefinsulfonates, are composed of ca. 60% by weight of alkanesulfonates and ca. 40% by weight of hydroxyalkanesulfonates; of these, about 80 to 85% by weight are monosulfonates and 15 to 20% by weight are disulfonates.

Preferred methyl ester sulfonates (MES) are obtained by sulfonation of the fatty acid methyl esters of plant or animal fats or oils. Preference is given to methyl ester sulfonates from plant fats and oils, e.g. from rapeseed oil, sunflower oil, soya oil, palm oil, coconut fat, etc.

Preferred sarcosinates are sodium lauroyl sarcosinate or sodium stearoyl sarcosinate.

Preferred protein fatty acid condensates are plant products based on wheat.

Preferred alkyl phosphates are mono- and diphosphoric acid alkyl esters.

Acyl Glutamate

In a specific embodiment, component b) comprises at least 30% by weight, particularly at least 50% by weight, in particular at least 75% by weight, and more specifically at least 90% by weight, of at least one acyl glutamate. In a specific embodiment, component b) consists exclusively of at least one acyl glutamate.

Acyl glutamates suitable as component b) are compounds of formula (I)

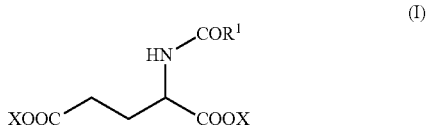

wherein $COR^1$ is a linear or branched acyl radical having 6 to 22 carbon atoms and 0, 1, 2 or 3 double bonds and X is hydrogen, an alkali metal, the monovalent charge equivalent of an alkaline earth metal, ammonium, alkylammonium, alkanolammonium or glucammonium. The preparation of acyl glutamates takes place for example by Schotten-Baumann acylation of glutamic acid with fatty acids, fatty acid esters or fatty acid halides. Acyl glutamates are commercially available for example from Clariant AG, Frankfurt/DE, or Ajinomoto Co. Inc., Tokyo/JP. An overview of the preparation and properties of acyl glutamates can be found by M. Takehara et al. in J. Am. Oil Chem. Soc. 49 (1972) 143. Typical acyl glutamates suitable as component b) are preferably derived from fatty acids having 6 to 22 and particularly preferably 12 to 18 carbon atoms. In particular, the mono- or dialkali metal salts of the acyl glutamate are used. These include e.g. (tradenames of Ajinomoto, USA in brackets): sodium cocoyl glutamate (Amisoft CS-11), disodium cocoyl glutamate (Amisoft ECS-22SB), triethanolammonium cocoyl glutamate (Amisoft CT-12), triethanolammonium lauroyl glutamate (Amisoft LT-12), sodium myristoyl glutamate (Amisoft MS-11), sodium stearoyl glutamate (Amisoft HS-11 P) and mixtures thereof.

Particular preference is given to acyl glutamates which are derived from fatty acids having 10 to 18 carbon atoms, in particular acyl glutamates which are derived from fatty acids having 18 carbon atoms (stearoyl glutamates). Particular preference is given to sodium salts of stearoyl glutamate (INCI: Sodium Stearoyl Glutamate), as are sold, for example, under the tradename Eumulgin® SG (BASF Personal Care and Nutrition GmbH), or Amisoft HS-11 P® (Ajinomoto, USA). Particular preference is also given to acyl glutamates which are derived from fatty acid mixtures having 10 to 18 carbon atoms, specifically cocoyl glutamates. Particular preference is given to the sodium salts of the sodium cocoyl glutamate.

In a specific embodiment, component b) consists exclusively of at least one stearoyl glutamate. In a further specific embodiment, component b) consists exclusively of at least one cocoyl glutamate.

Alkyl Sulfates

In a another specific embodiment, component b) comprises at least 30% by weight, particularly at least 50% by weight, in particular at least 75% by weight, and especially at least 90% by weight, of at least one alkyl sulfate. In a specific embodiment, component b) consists exclusively of at least one alkyl sulfate.

As component b), preference is given to using at least one sulfate of a fatty alcohol of the general formula $R^2$—O—$SO_3Y$, in which $R^2$ is a linear or branched, saturated or unsaturated hydrocarbon radical having 6 to 22 carbon atoms and Y is an alkali metal, the monovalent charge equivalent of an alkaline earth metal, ammonium, mono-, di-, tri- or tetraalkylammonium, alkanolammonium or glucammonium. Suitable fatty alcohol sulfates are preferably obtained by sulfation of native fatty alcohols or synthetic oxo alcohols and subsequent neutralization. Typical examples of fatty alcohol sulfates are the sulfation products of caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, behenyl alcohol and elaeostearyl alcohol, and also the salts and mixtures thereof. Preferred salts of the fatty alcohol sulfates are the sodium and potassium salts, in particular the sodium salts. Preferred mixtures of the fatty alcohol sulfates are based on technical-grade alcohol mixtures which are produced e.g. during the high-pressure hydrogenation of technical-grade methyl esters based on fats and oils or during the hydrogenation of aldehydes from the oxo synthesis or during the dimerization of unsaturated fatty alcohols. To provide the alkyl sulfates used as component b), preference is given to using fatty alcohols and fatty alcohol mixtures having 12 to 18 carbon atoms and in particular 16 to 18 carbon atoms. Typical examples thereof are technical-grade alcohol sulfates based on plant raw materials.

In one or more embodiments, component b) comprises at least one sulfate of a $C_{16}/C_{18}$-fatty alcohol mixture or a salt thereof. In one or more specific embodiments, component b) comprises, or consists of, sodium cetearyl sulfate (cetearyl refers to a mixture of cetyl (hexadecyl) and stearyl (octadecyl)).

Sodium cetearyl sulfate is commercially available under the name Lanette E from BASF Personal Care and Nutrition GmbH as a 1:1 mixture of sodium cetyl sulfate and sodium stearyl sulfate.

Component c)

In one or more embodiments, the composition comprises component c) in an amount of from 10 to 95% by weight, particularly 20 to 90% by weight, and more particularly 25 to 85% by weight, based on the total weight of components a), b) and c).

In one or more embodiments, fatty alcohols suitable as component c) have 8 to 30 carbon atoms, particularly 10 to 22 carbon atoms, and in particular 12 to 20 carbon atoms. The hydrocarbon radical of the fatty alcohols can in principle be linear or branched, saturated or unsaturated. Typical examples of fatty alcohols are caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol and mixtures thereof. Preferred mixtures of the fatty alcohols are based on technical-grade alcohol mixtures which are produced e.g. during the high-pressure hydrogenation of technical-grade methyl esters based on fats and oils or during the hydrogenation of aldehydes from the oxo synthesis or during the dimerization of unsaturated fatty alcohols.

In one or more specific embodiments, component c) comprises a $C_{16}/C_{18}$-fatty alcohol mixture.

Cetylstearyl alcohol is commercially available under the name Lanette O® from BASF Personal Care and Nutrition GmbH as 1:1 mixture of the two individual $C_{16}$- and $C_{18}$-alcohols.

In one or more embodiments, the quantitative weight ratio of component a) (=lecithin) to component b) (=anionic surfactant) is in a range from 5:1 to 1:5, particularly 4:1 to 1:4, and in particular 3:1 to 1:1. In a specific embodiment, the quantitative weight ratio of component a) to component b) is in a range from about 2.5:1 to 1.5:1.

Solid Composition

In one or more embodiments, components a), b) and c) can advantageously be formulated to give a solid composition. This comprises the lecithin together with an emulsifying and a consistency-imparting component and is exceptionally suitable e.g. for producing aqueous hair conditioners. It is therefore specifically suitable as intermediate for producing hair cosmetic compositions. It is also suitable as one component of a "kit of parts" composition for formulating a hair cosmetic composition.

The invention therefore further provides a solid composition consisting of a) at least one plant lecithin, b) at least one anionic surfactant, and c) at least one fatty alcohol, where components a), b) and c) are as defined above.

In one or more embodiments, provided is a solid composition consisting of
- 4 to 60% by weight of component a),
- 1 to 30% by weight of component b), and
- 10 to 95% by weight of component c), wherein the total weight of components a), b) and c) adds up to 100% by weight.

The solid compositions according to the invention can be produced for example by melt granulation or melt pelleting. Here, a mixture of components a), b) and c) is heated with stirring in a mixer for example. The heating can take place in a customary manner, e.g. by means of heating mantle, with microwaves, radiation energy or else via the input of energy of the stirrer. If the melting temperature of the mixture used in each case is achieved or its surface softens or starts to melt, granulation starts. Then, the warm melt granules are either discharged from the mixer and cooled in thin layers at room temperature, or else are cooled with suitable cooling (e.g. cooling mantle) in the mixer, possibly with stirring. To produce pellets, the melt can be discharged from the mixer onto a chilled roller or a chilled conveyor belt. Alternatively, to produce granules or pellets, an extruder can be used. The constituents of the composition can all or in part be premixed in a container. The mixing of all components, individual components and the non-premixed components are fed to the extruder and brought to the desired consistency. To produce pellets, the extruder product can be converted to a round form e.g. in a spheronizer. To produce granules, the extruder product can be conveyed further e.g. to a fluidized bed.

Hair Cosmetic Composition

In one or more embodiments, the hair cosmetic composition comprises component a) in an amount of from 0.2 to 20% by weight, particularly 0.4 to 10% by weight, and in particular 0.6 to 5% by weight, based on the total weight of the cosmetic composition.

In one or more embodiments, the hair cosmetic composition comprises component b) in an amount of from 0.1 to 10% by weight, particularly 0.2 to 5% by weight, and in particular 0.3 to 2.5% by weight, based on the total weight of the cosmetic composition.

In one or more embodiments, the hair cosmetic composition comprises component c) in an amount of from 0.5 to 50% by weight, particularly 1 to 25% by weight, and in particular 1.5 to 15% by weight, based on the total weight of the cosmetic composition.

In one or more embodiments, the hair cosmetic compositions comprise at least one further component which is selected from:
d) surfactants different from components a) to c),
e) cosmetically acceptable active ingredients,
f) cosmetically acceptable auxiliaries different from components a) to e),
g) water.

Further Surfactants d)

In one suitable embodiment, the hair cosmetic composition according to the invention comprises at least one further surfactant d). In one or more embodiments, the hair cosmetic composition comprises at least one further surfactant d) in an amount of from 0.05 to 5% by weight, particularly 0.1 to 2.5% by weight, and in particular 0.2 to 2% by weight, based on the total weight of the cosmetic composition.

In one or more embodiments, the total amount of at least one anionic surfactant b) and at least one further surfactant d) is in a range from 0.1 to 10% by weight, particularly 0.2 to 5% by weight, and in particular 0.3 to 2.5% by weight, based on the total weight of the cosmetic composition.

In one specific embodiment, the hair cosmetic composition according to the invention comprises no further surfactant d).

Suitable further surfactants d) are selected from phospholipids different from lecithin, nonionic surfactants, amphoteric surfactants, cationic surfactants and mixtures thereof.

Phospholipids are phosphorus-containing amphiphilic lipids. Phospholipids suitable as component d) which occur in lecithin only in a minor amount, if at all, are e.g. phosphatidylserines, sphingomyelins and plasmalogens. Sphingomyelins are derived from sphingosine as basic backbone and plasmalogens differ from phosphoglycerides only in that they carry an unsaturated alcohol (e.g. $-O-CH=CH-(CH_2)_n-CH_3$) linked via an ether bridge on the $C_1$ atom of the glycerol instead of a fatty acid. Also suitable are the so-called lysophospholipids in which a fatty acid radical has been separated off from the phospholipid molecule to give an OH group, e.g. with the help of a phospholipase.

The nonionic surfactants include, for example:
fatty alcohol polyoxyalkylene esters, for example lauryl alcohol polyoxyethylene acetate,
alkyl polyoxyalkylene ethers which are derived from low molecular weight $C_1$-$C_6$-alkohols or from $C_7$-$C_{30}$-fatty alcohols. Here, the ether component can be derived from ethylene oxide units, propylene oxide units, 1,2-butylene oxide units, 1,4-butylene oxide units and random copolymers and block copolymers thereof. These include specifically fatty alcohol alkoxylates and oxo alcohol alkoxylates, in particular of the type RO—$(R_{18}O)_r(R_{19}O)_sR_{20}$ where $R_{18}$ and $R_{19}$, independently of one another, $=C_2H_4$, $C_3H_6$, $C_4H_8$ and $R_{20}$=H, or $C_1$-$C_{12}$-alkyl, R=$C_3$-$C_{30}$-alkyl or $C_6$-$C_{30}$-alkenyl, r and s, independently of one another, are 0 to 50, where both cannot be 0, such as isotridecyl alcohol and oleyl alcohol polyoxyethylene ethers,
alkylaryl alcohol polyoxyethylene ethers, e.g. octylphenol polyoxyethylene ethers,
alkoxylated animal and/or plant fats and/or oils, for example corn oil ethoxylates, castor oil ethoxylates, tallow fat ethoxylates,
glycerol esters, such as, for example, glycerol monostearate,
alkylphenol alkoxylates, such as, for example, ethoxylated isooctyl-, octyl- or nonylphenol, tributylphenol polyoxyethylene ether,
fatty amine alkoxylates, fatty acid amide and fatty acid diethanolamide alkoxylates, in particular ethoxylates thereof,
sugar surfactants, sorbitol esters, such as, for example, sorbitan fatty acid esters (sorbitan monooleate, sorbitan tristearate), polyoxyethylene sorbitan fatty acid esters, alkyl polyglycosides, N-alkylgluconamides,
alkyl methyl sulfoxides,
alkyl dimethyl phosphine oxides, such as, for example, tetradecyl dimethyl phosphine oxide.

Suitable amphoteric surfactants are e.g. alkylbetaines, alkylamidopropylbetaines, alkylsulfobetaines, alkyl glycinates, alkyl carboxyglycinates, alkyl amphoacetates or propionates, alkyl amphodiacetates or dipropionates. For example, it is possible to use cocodimethylsulfopropylbetaine, laurylbetaine, cocamidopropylbetaine, sodium cocamphopropionate or tetradecyldimethylamine oxide.

The cationic surfactants include, for example, quaternized ammonium compounds, in particular alkyltrimethylammonium and dialkyldimethylammonium halides and alkyl sulfates, and pyridine and imidazoline derivatives, in particular alkylpyridinium halides. For example, behenyl or cetyltrimethylammonium chloride can be used.

In one specific embodiment, the hair cosmetic compositions according to the invention comprise no cationic surfactant.

Active Ingredients e)

Suitable cosmetically and/or dermatologically active ingredients e) are e.g. antidandruff active ingredients, proteins and protein derivatives, cosmetically active polymers, hair pigmentation agents, bleaches, keratin-hardening substances, antimicrobial active ingredients, light filter active ingredients, repellent active ingredients, hyperemic substances, antiphlogistics, keratinizing substances, antioxidative active ingredient and/or free radical active ingredients, sebostatic active ingredients, plant extracts, antierythematous or antiallergic active ingredients and mixtures thereof.

The hair cosmetic compositions according to the invention can comprise, as active ingredient e) (and also optionally as auxiliary f)), at least one antidandruff active ingredient.

Suitable antidandruff active ingredients are piroctone olamine (1-hydroxy-4-methyl-6-(2,4,4-trimethylpentyl)-2-(1H)-pyridinonemonoethanolamine salt), crinipan AD (climbazole), ketoconazole, (4-acetyl-1-{4-[2-(2,4-dichlorophenyl) r-2-(1H-imidazol-1-ylmethyl)-1,3-dioxalan-c-4-ylmethoxyphenyl}piperazine, ketoconazole, elubiol, selenium disulfide, sulfur colloidal, sulfur polyethylene glycol sorbitan monooleate, sulfur ricinol polyethoxylate, sulfur tar distillates, salicylic acid (or in combination with hexachlorophene), undecylenic acid monoethanolamide sulfosuccinate Na salt, lamepon UD (protein-undecylenic acid condensate), zinc pyrithione, aluminum pyrithione and magnesium pyrithione/dipyrithione magnesium sulfate.

Active ingredients e) which can be used are also proteins and protein derivatives, such as, e.g. protein condensates or protein hydrolyzates.

The compositions according to the invention can comprise at least one polymer as cosmetic active ingredient e) (and also optionally as auxiliary f)). These include quite generally anionic, cationic, amphoteric and neutral polymers.

Examples of anionic polymers are copolymers of acrylic acid and acrylamide and salts thereof; sodium salts of polyhydroxycarboxylic acids, water-soluble or water-dispersible polyesters, polyurethanes, e.g. Luviset PUR® from BASF, and polyureas. Particularly suitable polymers are copolymers of t-butyl acrylate, ethyl acrylate, methacrylic acid (e.g. Luvimer® 100P), copolymers of ethyl acrylate and methacrylic acid (e.g. Luvimer® MAE), copolymers of N-tert-butyl acrylamide, ethyl acrylate, acrylic acid (Ultrahold® 8, strong), copolymers of vinyl acetate, crotonic acid and optionally further vinyl esters (e.g. Luviset® grades), maleic anhydride copolymers, optionally reacted with alcohol, anionic polysiloxanes, e.g. carboxy functional ones, t-butyl acrylate, methacrylic acid (e.g. Luviskol® VBM), copolymers of acrylic acid and methacrylic acid with hydrophobic monomers, such as e.g. $C_4$-$C_{30}$-alkyl esters of (meth) acrylic acid, $C_4$-$C_{30}$-alkyl vinyl esters, $C_4$-$C_{30}$-alkyl vinyl ether and hyaluronic acid. One example of an anionic polymer is also the methyl methacrylate/methacrylic acid/acrylic acid/urethane acrylate copolymer available under the name Luviset® Shape (INCI Name: Polyacrylate-22). Examples of anionic polymers are also vinyl acetate/crotonic acid copolymers as are commercially available for example under the names Resyn® (National Starch) and Gafset® (GAF), and vinylpyrrolidone/vinyl acrylate copolymers, obtainable for example under the tradename Luviflex® (BASF). Further suitable polymers are the vinylpyrrolidone/acrylate terpolymer available under the name Luviflex® VBM-35 (BASF) and sodium sulfonate-containing polyamides or sodium sulfonate-containing polyesters. Also of suitability are vinylpyrrolidone/ethyl methacrylate/methacrylic acid copolymers, as are sold by Stepan under the name Stepanhold-Extra and -R1, and the Carboset® grades from BF Goodrich.

Suitable cationic polymers are e.g. cationic polymers with the INCI name Polyquaternium, e.g. copolymers of vinylpyrrolidone/N-vinylimidazolium salts (Luviquat® FC, Luviquat® HM, Luviquat® MS, Luviset Clear®, Luviquat Supreme®, Luviquat® Care), copolymers of N-vinylpyrrolidone/dimethylaminoethyl methacrylate, quaternized with diethyl sulfate (Luviquat® PQ 11), copolymers of N-vinyl-caprolactam/N-vinylpyrrolidone/N-vinylimidazolium salts (Luviquat® Hold); cationic cellulose derivatives (polyquaternium-4 and -10), acrylamide copolymers (polyquaternium-7) and chitosan. Suitable cationic (quaternized) polymers are also Merquat® (polymer based on dimethyldiallylammonium chloride), Gafquat® (quaternary polymers which are formed by the reaction of polyvinylpyrrolidone with quaternary ammonium compounds), polymer JR (hydroxyethylcellulose with cationic groups) and plant-based cationic polymers, e.g. guar polymers, such as the Jaguar® grades from Rhodia.

Very particularly suitable polymers are neutral polymers, such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include, for example, Luviflex® Swing (partially saponified copolymer of polyvinyl acetate and polyethylene glycol, BASF).

Suitable polymers are also nonionic, water-soluble or water-dispersible polymers or oligomers, such as polyvinylcaprolactam, e.g. Luviskol® Plus (BASF SE), or polyvinylpyrrolidone and copolymers thereof, in particular with vinyl esters, such as vinyl acetate, e.g. Luviskol® VA 37, VA 55, VA 64, VA 73 (BASF SE); polyamides, e.g. based on itaconic acid and aliphatic diamines, as are described e.g. in DE-A-43 33 238.

Suitable polymers are also amphoteric or zwitterionic polymers, such as the octylacrylamide/methyl methacrylate/tert-butylaminoethyl methacrylate/2-hydroxypropyl methacrylate copolymers available under the names Amphomer® (National Starch), and also zwitterionic polymers, as are disclosed for example in the German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Furthermore suitable zwitterionic polymers are methacroylethyl-betaine/methacrylate copolymers which are commercially available under the name Amersette® (AMERCHOL), and copolymers of hydroxyethyl methacrylate, methyl methacrylate, N,N-dimethylaminoethyl methacrylate and acrylic acid (Jordapon®).

Suitable polymers are also nonionic, siloxane-containing, water-soluble or -dispersible polymers, e.g. polyethersiloxanes, such as Tegopren® (Goldschmidt) or Belsil® (Wacker).

In one specific embodiment, the hair cosmetic compositions according to the invention comprise no siloxane-containing polymers.

Suitable antiphlogistics, which counteract skin irritations, are e.g. allantoin, bisabolol, dragosantol, chamomile extract, panthenol, etc. Suitable plant antiphlogistics are e.g. bromelain, willow bark, chamomile flowers, marigold flowers, arnica flowers, devil's claw root, ash bark, poplar bark, goldenrod, horse chestnut and incense.

Suitable keratin-hardening substances are generally active ingredients as are also used in antiperspirants, such as e.g. potassium aluminum sulfate, aluminum hydroxy chloride, aluminum lactate, etc.

Suitable photo filter active ingredients are substances which absorb UV rays in the UV-B and/or UV-A region in order to avoid hair damage. Suitable UV filters are those mentioned above. Also suitable are p-aminobenzoic acid esters, cinnamic acid esters, benzophenones, camphor derivatives, and also pigments which stop UV rays, such as titanium dioxide, talc and zinc oxide.

Suitable repellent active ingredients are compounds which are able to keep or drive certain animals, in particular insects, away from a person. These include e.g. 2-ethyl-1,3-hexanediol, N,N-diethyl-m-toluamide etc.

Suitable hyperemic substances, which stimulate circulation in the skin, are e.g. essential oils, such as dwarf pine needle, lavender, rosemary, juniper berry, horse chestnut extract, birch leaf extract, hayflower extract, ethyl acetate, camphor, menthol, peppermint oil, rosemary extract, eucalyptus oil, etc.

Cosmetically Acceptable Auxiliaries f)

The preparations according to the invention can also comprise at least one cosmetically acceptable auxiliary f). In one or more embodiments, the auxiliary f) is selected from oil bodies, fats, waxes, pearlescent waxes, propellants, consistency regulators, thickeners, superfatting agents, stabilizers, polymers, silicone compounds, UV stabilizers, antioxidants, film formers, swelling agents, hydrotropes, solubilizers, preservatives, perfume oils, dyes, etc. and mixtures thereof.

Especially suitable cosmetically compatible oil and/or fat components are described in Karl-Heinz Schrader, Grundlagen and Rezepturen der Kosmetika [Fundamentals and formulations of cosmetics], 2nd Edition, Verlag Hüthig, Heidelberg, pp. 319-355, to which reference is hereby made.

Oil Bodies

In one or more embodiments, the oil bodies are selected from:

Guerbet alcohols based on fatty alcohols having 6 to 18, preferably 8 to 10 carbon atoms, esters of linear or branched $C_6$-$C_{22}$-fatty acids with linear or branched $C_6$-$C_{22}$-fatty alcohols. These include e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate.

These include specifically also the esters of linear $C_6$-$C_{22}$-fatty acids with branched alcohols, in particular esters of 2-ethyl-hexanol, esters of $C_8$-$C_{30}$-alkylhydroxycarboxylic acids with linear or branched $C_6$-$C_{22}$-fatty alcohols in particular dioctyl malate, esters of linear and/or branched fatty acids with polyhydric alcohols (such as e.g. propylene glycol, dimerdiol or trimertriol) or Guerbet alcohols, liquid mono-, di- and triglycerides based on $C_6$-$C_{22}$-fatty acids and mixtures thereof, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having to 1 to 22 carbon atoms or polyols having 2 to 10 carbon atoms and 2 to 6 hydroxyl groups, plant oils such as palm oil, rapeseed oil, castor oil, coconut oil, evening primrose oil, corn germ oil, soybean oil, linseed oil, olive oil, peanut oil, safflower oil, sesame seed oil, grapefruit oil, basil oil, apricot oil, ginger oil, geranium oil, orange oil, rosemary oil, *macadamia* oil, onion oil, mandarin oil, pine oil, sunflower oil, oxidized plant oils, hydrogenated plant oils such as hydrogenated palm oil, hydrogenated rapeseed oil or hydrogenated soybean oil, animal oils such as pig fat oil, fish oils, dialkylamides of medium- to long-chain fatty acids, e.g. Hallcomids, plant oil esters, such as rapeseed oil methyl ester, linear and branched $C_6$-$C_{22}$-fatty alcohol carbonates, such as e.g. dicaprylyl carbonate (Cetiol CC), Guerbet carbonates based on fatty alcohols have 6 to 18, preferably 8 to 10, carbon atoms, esters of benzoic acid with linear and/or branched $C_6$-$C_{22}$-alcohols (e.g. Finsolv TN), linear or branched, symmetrical or asymmetrical dialkyl ethers having 6 to 22 carbon atoms per alkyl group, such as e.g. dicaprylyl ether (Cetiol OE), ring-opening products of epoxidized fatty acid esters with polyols, silicone oils (cyclomethicones, silicon methicone grades, etc.), aliphatic or naphthenic hydrocarbons, such as e.g. squalane, squalene or dialkylcyclohexanes, in consideration.

paraffin oils, aromatic hydrocarbons and aromatic hydrocarbon mixtures, e.g. xylenes, Solvesso 100, 150 or 200, and the like, carboxylic acid esters, e.g. adipic acid dialkyl esters such as bis(2-ethylhexyl) adipate, phthalic acid dialkyl esters such as bis(2-ethylhexyl) phthalate.

Fats and Waxes

Typical examples of fats are glycerides, i.e. solid or liquid, plant or animal products which consist essentially of mixed glycerol esters of higher fatty acids, suitable waxes are inter alia natural waxes, such as e.g. candelilla wax, carnauba wax, Japan wax, espartograss wax, cork wax, guaruma wax, rice germ oil wax, sugarcane wax, ouricury wax, montan wax, beeswax, shellac wax, spermaceti, lanoline (wool wax), uropygial grease, ceresin, ozokerite (earth wax), petrolatum, paraffin waxes, microwaxes; chemically modified waxes (hard waxes), such as e.g. montan ester waxes, sasol waxes, hydrogenated jojoba waxes, and also synthetic waxes, such as e.g. polyalkylene waxes and polyethylene glycol waxes.

Pearlescent Waxes

Suitable pearlescent waxes are, for example: alkylene glycol esters, specifically ethylene glycol distearate; fatty acid alkanolamides, specifically coconut fatty acid diethanolamide; partial glycerides, specifically stearic acid monoglyceride; esters of polyhydric, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have in total at least 24 carbon atoms, especially laurone and distearyl ether; fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Propellants

Propellants are the propellants customarily used for hair sprays or aerosol foams. Preference is given to mixtures of propane/butane, pentane, dimethyl ether, 1,1-difluoroethane (HFC-152a), carbon dioxide, nitrogen or compressed air.

Consistency Regulators and Thickeners

Suitable consistency regulators are primarily fatty alcohols or hydroxy fatty alcohols having 12 to 22 and preferably 16 to 18 carbon atoms and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and tyloses, carboxymethylcellulose and hydroxyethyl- and hydroxypropylcellulose, also relatively high molecular weight polyethylene glycol mono- and diesters of fatty acids, polyacrylates (e.g. Carbopoles and Pemulen grades from Noveon; synthalens from Sigma; Keltrol grades from Kelco; Sepigel grades from Seppic; Salcare grades Allied Colloids), polyacrylamides, polymers, polyvinyl alcohol and polyvinylpyrrolidone. Bentonites have also proven to be particularly effective, such as, e.g. Bentone Gel VS-5PC (Rheox), which is a mixture of cyclopentasiloxane, disteardimonium hectorite and propylene carbonate. Further suitable surfactants, such as, for example ethoxylated fatty acid glycerides, esters of fatty acids with polyols, such as, for example, pentaerythritol or trimethylolpropane, fatty alcohol ethoxylates with a narrowed homolog distribution or alkyl oligoglucosides, and also electrolytes, such as sodium chloride and ammonium chloride. Furthermore, mention may also be made of sodium polynaphthalenesulfates, acrylate/aminoacrylate/C10-30-alkyl PEG-20 itaconate copolymers and polyacrylamidomethylpropanesulfonic acid.

Suitable polymeric thickeners are, for example, optionally modified polymeric natural substances (carboxymethylcellulose and other cellulose ethers, hydroxyethyl- and -propylcellulose and the like), and also synthetic polymeric thickeners (polyacrylic and polymethacrylic compounds, vinyl polymers, polycarboxylic acids, polyethers, polyimines, polyamides). These include the polyacrylic and polymethacrylic compounds which have in part already been specified previously, for example the high molecular weight homopolymers of acrylic acid crosslinked with a polyalkenyl polyether, in particular an allyl ether of sucrose, pentaerythritol or propylene, (INCI name: Carbomer). Such polyacrylic acids are available inter alia from BF Goodrich under the tradename Carbopol®, e.g. Carbopol 940 (molecular weight ca. 4 000 000), Carbopol 941 (molecular weight ca. 1 250 000) or Carbopol 934 (molecular weight ca. 3 000 000). Also included are acrylic acid copolymers as are available for example from Rohm & Haas under the tradenames Aculyn® and Acusol®, e.g. the anionic, non-associative polymers Aculyn 22, Aculyn 28, Aculyn 33 (crosslinked), Acusol 810, Acusol 823 and Acusol 830 (CAS 25852-37-3). Also of specific suitability are associative thickeners, e.g. based on modified polyurethanes (HEUR) or hydrophobically modified acrylic or methacrylic acid copolymers (HASE thickeners, High Alkali Swellable Emulsion).

The use amount of the additional thickeners is preferably in a range from 0.001 to 5% by weight, preferably 0.1 to 3%, based on the total weight of the composition.

Superfatting Agents

Superfatting agents which can be used are substances such as, for example, lanoline, and also polyethoxylated or acylated lanoline derivatives, polyol fatty acid esters, monoglycerides and fatty acid alkanolamides, the latter simultaneously serving as foam stabilizers.

Stabilizers

Stabilizers which can be used are metal salts of fatty acids, such as e.g. magnesium, aluminum and/or zinc stearate or ricinoleate.

Film Formers

Customary film forms are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid or salts thereof and similar compounds.

Swelling Agents

Swelling agents for aqueous phases which can be used are montmorillonites, clay mineral substances, Pemulen, and also alkyl-modified Carbopol grades (Noveon).

Hydrotropes

To improve the flow behavior, hydrotropes, such as, for example, ethanol, isopropyl alcohol, or polyols, can also be used. Polyols which are contemplated here have preferably 2 to 15 carbon atoms and at least two hydroxyl groups. The polyols can also comprise further functional groups, in particular amino groups, and/or be modified with nitrogen. Typical examples are glycerol; alkylene glycols, such as, for example, ethylene glycol, diethylene glycol, propylene glycol, butylene glycol, hexylene glycol, and also polyethylene glycols with an average molecular weight of from 100 to 1000 daltons; technical-grade oligoglycerol mixtures with a degree of self-condensation of from 1.5 to 10, such as, for example, technical-grade diglycerol mixtures with a diglycerol content of from 40 to 50% by weight; methylol compounds, such as in particular trimethylolethane, trimethylolpropane, trimethylolbutane, pentaerythritol and dipentaerythritol; lower alkyl glucosides, in particular those with 1 to 8 carbon atoms in the alkyl radical, such as, for example, methyl and butyl glucoside; sugar alcohols having 5 to 12 carbon atoms, such as, for example, sorbitol or mannitol, sugar having 5 to 12 carbon atoms, such as, for example, glucose or sucrose; amino sugars, such as, for example, glucamine; dialcoholamines, such as diethanolamine or 2-amino-1,3-propanediol.

Preservatives

Suitable preservatives are, for example, phenoxyethanol, formaldehyde solution, parabens, pentanediol or sorbic acid, and also the silver complexes known under the name Surfacine.

Perfume Oils and Aromas

Perfume oils which may be mentioned are mixtures of natural and synthetic fragrances. Natural fragrances are extracts from flowers (lily, lavender, rose, jasmine, neroli, ylang ylang), stems and leaves (geranium, patchouli, petitgrain), fruits (anise, coriander, caraway, juniper), fruit peels (bergamot, lemon, oranges), roots (mace, angelica, celery, cardamom, *costus*, iris, calmus), woods (pinewood, sandalwood, guaiacwood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Animal raw materials are also suitable, such as, for example, civet and castoreum. Typical synthetic fragrance compounds are products of the ester, ether, aldehyde, ketone, alcohol and hydrocarbon types. Fragrance compounds of the ester type are e.g. benzyl acetate, phenoxyethyl isobutyrate, p-tert-butyl cyclohexyl acetate, linalyl acetate, dimethylbenzyl carbinyl acetate, phenyl ethyl acetate, linalyl benzoate, benzyl formate, ethylmethyl phenyl glycinate, allyl cyclohexyl propionate, styrallyl propionate and benzyl salicylate. The ethers include, for example, benzyl ethyl ether; the aldehydes include e.g. the linear alkanals having 8 to 18 carbon atoms, citral, citronellal, citronellyloxyacetaldehyde, cyclamenaldehyde, hydroxycitronellal, lilial and bourgeonal, the ketones include e.g. the ionones, isomethylionone and methyl cedryl ketone, the alcohols include anethole, citronellol, eugenol, isoeugenol, geraniol, linalool, phenylethyl alcohol and terpineol, the hydrocarbons include primarily the terpenes and balsams. However, preference is given to using mixtures of different fragrances which together produce a pleasant scent note. Essential oils of relatively low volatility, which are mostly used as aroma components, are also suitable as perfume oils, e.g. sage oil, chamomile oil, clove oil, melissa oil, mint oil, cinnamon leaf oil, linden blossom oil, juniper berry oil, vetiver oil, olibanum oil, galbanum oil, labolanum oil and lavandine oil. Preferably, bergamot oil, dihydromyrcenol, lilial, lyral, citronellol, phenylethyl alcohol, hexylzimtaldehyde, geraniol, benzylacetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, -damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillate, irotyl and floramat, alone or in mixtures, are used.

Suitable aromas are, for example, peppermint oil, spearmint oil, anise oils, star anise oil, caraway oil, eucalyptus oil, fennel oil, lemon oil, wintergreen oil, clove oil, menthol and the like.

Dyes

Dyes which can be used are the substances approved and suitable for cosmetic purposes. Examples are cochineal red A (C.I. 16255), patent blue V (C.I. 42051), indigo tin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. These dyes are usually used in concentrations of from 0.001 to 0.1% by weight, based on the total mixture.

Preferably, the hair treatment compositions according to the invention are in the form of a hair rinse, hair mask, shampoo, hair spray, hair foam, hair mousse, hair gel, setting foam, hair tonic, hair setting composition, end fluid, neutralizer for permanent waves, hair colorant and hair bleach or "hot-oil-treatments". Hair sprays can be in the form of aerosol sprays or pump sprays without propellant gas. Hair foams can be present as aerosol foams or pump foams without propellant gas.

Depending on the field of application, the hair cosmetic preparations can be applied as (aerosol) spray, (aerosol) foam, gel, gel spray, cream, lotion or wax. Hair sprays and hair foams preferably comprise predominantly or exclusively water-soluble or water-dispersible components. If the compounds used in the hair sprays and hair foams according to the invention are water-dispersible, they can be used in the form of aqueous microdispersions with particle diameters of usually 1 to 350 nm, preferably 1 to 250 nm. The solids contents of these preparations are here usually in a range from about 0.5 to 20% by weight.

In one or more embodiments, the hair cosmetic composition comprises at least one cosmetically acceptable carrier. In one or more embodiments, the carrier component is selected from
  i) water,
  ii) water-miscible organic solvents, preferably $C_2$-$C_4$-alkanols, in particular ethanol,
  iii) oils, fats, waxes,
  iv) esters of $C_6$-$C_{30}$-monocarboxylic acids with mono-, di- or trihydric alcohols that are different from iii),
  v) saturated acyclic and cyclic hydrocarbons,
  vi) fatty acids,
  vii) fatty alcohols,
  viii) propellant gases,
and mixtures thereof.

Suitable carriers are the corresponding aforementioned auxiliaries.

The hair cosmetic formulations according to the invention comprise, in one specific embodiment,
  A) 0.05 to 20% by weight of at least one lecithin component a),
  B) 0.1 to 10% by weight of at least one anionic surfactant component b),
  C) 0.5 to 50% by weight of at least one fatty alcohol component c),
  D) 20 to 99.95% by weight of at least one cosmetically acceptable carrier,
  E) 0 to 50% by weight of at least one propellant gas,
  F) 0 to 25% by weight of at least one cosmetically acceptable active ingredient,
  G) 0 to 25% by weight of at least one cosmetically acceptable auxiliary different from components A) to F),
with the proviso that components A) to G) add to 100% by weight.

The preparation of the hair cosmetic compositions according to the invention takes place by customary processes known to the person skilled in the art.

The following paragraphs are a list of embodiments of the present invention.

Embodiment 1 is a hair cosmetic composition comprising
a) at least one plant lecithin,
b) at least one anionic surfactant, and
c) at least one fatty alcohol.

Embodiment 2 is the composition according to embodiment 1, comprising
  4 to 60% by weight of component a),
  1 to 30% by weight of component b), and
  to 95% by weight of component c),
based on the total weight of components a), b) and c).

Embodiment 3 is the composition according to embodiment 1, where component a) consists, to at least 30% by weight, preferably to at least 50% by weight, in particular to at least 75% by weight, specifically to at least 90% by weight, based on the total weight of component a), of rapeseed lecithin.

Embodiment 4 is the composition according to any one of the preceding embodiments, where component a) consists exclusively of rapeseed lecithin.

Embodiment 5 is the composition according to any one of embodiments 1 to 4, where the anionic surfactant b) comprises at least one acyl glutamate or consists of at least one acyl glutamate.

Embodiment 6 is the composition according to embodiment 5, where the anionic surfactant b) comprises stearoyl glutamate and/or sodium cocoyl glutamate or consists of stearoyl glutamate and/or sodium cocoyl glutamate.

Embodiment 7 is the composition according to any one of embodiments 1 to 4, where the anionic surfactant b) comprises at least one alkyl sulfate or consists of at least one alkyl sulfate.

Embodiment 8 is the composition according to embodiment 7, where the anionic surfactant b) comprises sodium cetearyl sulfate or consists of sodiumcetearyl sulfate.

Embodiment 9 is the composition according to any one of the preceding embodiments, where the fatty alcohol c) comprises cetylstearyl alcohol or consists of cetylstearyl alcohol.

Embodiment 10 is the composition according to any one of the preceding embodiments, where the quantitative weight ratio of component a) to component b) is in a range from 5:1 to 1:5, preferably 4:1 to 1:4, particularly preferably 3:1 to 1:1.

Embodiment 11 is the composition according to any one of the preceding embodiments, which additionally comprises at least one further component which is selected from:
d) surfactants different from components a) to c),
e) cosmetically acceptable active ingredients,
f) cosmetically acceptable auxiliaries different from components a) to e),
g) water.

Embodiment 12 is the use of a composition comprising
a) at least one plant lecithin,
b) at least one anionic surfactant, and
c) at least one fatty alcohol,
where components a), b) and c) are as defined in any one of embodiments 3 to 10, in a hair treatment composition.

Embodiment 13 is the use according to embodiment 12 in hair treatment compositions as conditioner.

Embodiment 14 is the use according to embodiment 12 or 13, where the composition is in the form of a hair rinse, hair mask, shampoo, hair spray, hair foam, hair mousse, hair gel, hair tonic, hair setting composition, end fluid, neutralizer for permanent waves, hair colorant and bleach or hot-oil treatment.

Embodiment 15 is a solid composition consisting of
a) at least one plant lecithin,
b) at least one anionic surfactant, and
c) at least one fatty alcohol,
where components a), b) and c) are as defined in any one of embodiments 3 to 10.

Embodiment 16 is the solid composition according to Embodiment 15, consisting of
4 to 60% by weight of component a),
1 to 30% by weight of component b), and
10 to 95% by weight of component c),
where the total weight of components a), b) and c) adds up to 100% by weight.

Embodiment 17 is the solid composition according to either of embodiments 15 and 16 defined in the form of granules or in the form of pellets.

Embodiment 18 is the use of a solid composition as defined in any one of Embodiments 15 to 17 as intermediate for producing a hair cosmetic composition.

The invention is illustrated in more detail by reference to the following, non-limiting examples.

EXAMPLES

Example 1

Viscosity and Stability as a Function of the Emulsifier Used

Preparation of the test formulations according to Table 1:
2% by weight of rapeseed lecithin (Solec RF-10 from Solae), 4% by weight of cetearyl alcohol (Lanette O®=1:1 mixture of $C_{16}$- and $C_{18}$-alkohol), 1% by weight of emulsifier according to Table 1 and the corresponding amount of water ad 100% by weight were introduced as initial charge in a 1l vessel and homogenized using a paddle stirrer at 70 to 80° C. and stirred until cold. The viscosity was measured using a Brookfield viscometer with spindle 4 at 20° C. and 10 rpm.

TABLE 1

| Emulsifier | INCI name | Appearance | Viscosity [mPas] |
|---|---|---|---|
| Anionic | | | |
| Lanette E | Sodium Cetearyl Sulfate | homogeneous | 7000 |
| Emulgin SG | Sodium Stearoyl Glutamate | homogeneous | 5000 |
| Plantapon ACG | Sodium Cocoyl Glutamate | homogeneous | 5700 |
| Plantapon SUS | Disodium Lauryl Sulfosuccinate | homogeneous | 4000 |
| Eumulgin Prisma | Disodium Cetearyl Sulfosuccinate | homogeneous | 1400 |
| Arlatone SCI | Cocoyl-Isethionate | homogeneous | 5600 |
| Texapon N 70 | Sodium Laureth Sulfate | homogeneous | 5000 |
| Nonionic | | | |
| Plantacare 1200 | Lauryl Glucoside | inhomogeneous | unstable |
| Plantacare 810 | Caprylyl/Capryl Glucoside | inhomogeneous | unstable |
| Emulgade PL 68/50 | Cetearyl Glucoside and Cetearyl Alcohol | inhomogeneous | unstable |
| Eumulgin B 2 | Ceteareth-20 | inhomogeneous | unstable |
| Amphoteric | | | |
| Dehyton PK 45 | Cocoamidopropyl Betaine | homogeneous | unstable |
| Amphosol CDB | Cetyl Betaine | homogeneous | unstable |
| Cationic | | | |
| Dehyquart A | Cetrimonium Chloride | homogeneous | 3000 |
| Dehyquart S 18 | Stearamidopropyl Dimethylamine | inhomogeneous | unstable |

Example 2

Viscosity and Stability as a Function of the Emulsifier Used

According to the procedure from example 1, test formulations comprising 2% by weight of lecithin according to Table 2, 4% by weight of cetearyl alcohol (Lanette O®=1:1 mixture of $C_{16}$- and $C_{18}$-alcohol) and 1% by weight of Lanette E (sodium cetearyl sulfate) were prepared.

TABLE 2

| Phospholipid | Solec RF-10 [%] | Soy lecithin (India) [%] |
|---|---|---|
| Phosphatidylquoline (PC) | 15.49 | 15.08 |
| Phospatidylinisitol | 10.25 | 12.08 |
| Phosphatidylethanolamine (PE) | 7.84 | 11.3 |
| N-Acylphospatidylethanolamine | 0.60 | 1.53 |
| Phosphatidic acid | 4.28 | 6.16 |
| Phospholipid total | 42.93 | 48.79 |
| Phosphorus total | 1.79 | 1.99 |
| Iodine number | 83.7 | |
| PC:PE ratio | 1.98 | 1.33 |
| Viscosity [mPas] | 7200 | |
| Appearance of conditioner | homogeneous | inhomogeneous |

Example 3

Measuring the Zeta Potential

According to the procedure from example 1, test formulations comprising 2% by weight of rapeseed lecithin (Solec RF-10 from Solae), 4% by weight of Lanette O®, 1% by weight of emulsifier according to Table 3 and the corresponding amount of water ad 100% by weight were prepared. Measurement of the zeta potential was carried out using a Coulter DELSA 440 SX.

TABLE 3

| Emulsifier | pH | Zeta potential [mV] |
|---|---|---|
| Lanette E | 3.5 | −80 |
| Dehyquart A | 3.8 | +80 |

Example 4

Simultaneous Washing Tests

2% by weight of rapeseed lecithin (Solec RF-10 from Solae), 4% by weight of cetearyl alcohol (Lanette O®), 1% by weight of Lanette E®, (sodium cetearyl sulfate), 2% by weight of Myritol 312 (caprylic/capric triglyceride) and the corresponding amount of water ad 100% by weight were used to prepare a test formulation for a natural conditioner according to the invention. The pH was 3 to 4. As comparison conditioner, Logona Bio Daily Care hair rinse was used. Simultaneous hair washing experiments were carried out on 19 subjects, in each case treating one half of the head with the composition according to the invention and the other half with the comparison composition. Evaluation was carried out by means of grading by qualified people. The difference in the sensory assessment was given on a scale from −3 (great difference, comparison product better) to +3 (great difference, product according to the invention better). The product according to the invention was better by +1 (slightly improved) on the grading scale in the case of skin feel after rinsing, detangleability of wet hair, wet combability and feel to the touch of the wet hair. This is a significant improvement compared with the comparison product.

What is claimed is:

1. A solid composition consisting of
   a) at least one plant lecithin;
   b) at least one anionic surfactant; and
   c) at least one fatty alcohol;
   wherein the quantitative weight ratio of component a) to component b) is in a range from 3:1 to 1:1, and
   wherein component a) has a total phospholipid content of at least 35% by weight.

2. The solid composition according to claim 1, consisting of
   4 to 60% by weight of component a),
   1 to 30% by weight of component b), and
   10 to 95% by weight of component c),
   wherein the total weight of components a), b) and c) adds up to 100% by weight.

3. The solid composition according to claim 1, wherein the solid composition is in the form of granules or in the form of pellets.

4. A method of producing a hair cosmetic composition, the method comprising mixing the solid composition of claim 1 with at least one component selected from surfactants, cosmetically acceptable active ingredients, cosmetically acceptable auxiliaries, and water.

* * * * *